US008097212B2

(12) United States Patent
Cooper

(10) Patent No.: US 8,097,212 B2
(45) Date of Patent: Jan. 17, 2012

(54) DETECTION OF CONTAMINATION OF MUNICIPAL WATER DISTRIBUTION SYSTEMS

(75) Inventor: John F. Cooper, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 849 days.

(21) Appl. No.: 12/186,701

(22) Filed: Aug. 6, 2008

(65) Prior Publication Data
US 2008/0293042 A1 Nov. 27, 2008

(51) Int. Cl.
*E21B 47/18* (2006.01)
*G01N 29/04* (2006.01)
*H04B 13/00* (2006.01)

(52) U.S. Cl. ............. 422/68.1; 422/63; 422/67; 387/81; 387/82; 73/702

(58) Field of Classification Search ........................ None
See application file for complete search history.

(56) References Cited

U.S. PATENT DOCUMENTS

| | | | |
|---|---|---|---|
| 4,729,106 A | 3/1988 | Rush et al. | |
| 4,888,706 A | 12/1989 | Rush et al. | |
| 5,027,644 A | 7/1991 | Ziolkowski et al. | |
| 5,170,657 A | 12/1992 | Maresca, Jr. | |
| 5,333,502 A | 8/1994 | Clark, Jr. et al. | |
| 5,457,994 A | 10/1995 | Kwun et al. | |
| 5,869,748 A | 2/1999 | Stevenson et al. | |
| 5,983,736 A | 11/1999 | Gershman | |
| 5,987,990 A | 11/1999 | Worthington et al. | |
| 6,138,512 A | 10/2000 | Roberts et al. | |
| 6,155,292 A | 12/2000 | Kurata | |
| 6,173,074 B1 | 1/2001 | Russo | |
| 6,196,059 B1 | 3/2001 | Kosslinger et al. | |
| 6,290,908 B1 * | 9/2001 | Fukunaga et al. | ........... 422/68.1 |
| 6,429,650 B1 | 8/2002 | Kwun et al. | |
| 6,919,803 B2 * | 7/2005 | Breed | ........................ 340/539.14 |
| 7,001,106 B2 * | 2/2006 | Burnham et al. | ............. 405/157 |
| 2002/0189362 A1 | 12/2002 | Havlena | |

FOREIGN PATENT DOCUMENTS

| | | | |
|---|---|---|---|
| DE | 4037600 | * | 6/1992 |
| EP | 1 137 921 B1 | | 1/2003 |
| WO | WO 02/103303 A1 | | 12/2002 |
| WO | WO 2005/015789 | * | 2/2005 |

OTHER PUBLICATIONS

Foran, J. A., et al., "Early Warning Systems for Hazardous Biological Agents in Potable Water," EPH Online, Environmental Health Perspectives, vol. 108, No. 10, Oct. 2000, pp. 1-7.
"Making the Nation Safer, The Role of Science and Technology in Countering Terrorism," National Research Council, Prepublication copy, 2002, 6 pages.

(Continued)

Primary Examiner — P. Kathryn Wright
(74) Attorney, Agent, or Firm — Eddie E. Scott

(57) ABSTRACT

A system for the detection of contaminates of a fluid in a conduit. The conduit is part of a fluid distribution system. A chemical or biological sensor array is connected to the conduit. The sensor array produces an acoustic signal burst in the fluid upon detection of contaminates in the fluid. A supervisory control system connected to the fluid and operatively connected to the fluid distribution system signals the fluid distribution system upon detection of contaminates in the fluid.

3 Claims, 2 Drawing Sheets

OTHER PUBLICATIONS

"National Infrastructure Protection Center, Terrorist Interest in Water Supply and SCADA Systems" Information Bulletin 02-001, Jan. 29, 2002, 1 page.

Luthy, Richard G., "Water Supplies Need Better Protection," National Academy of Sciences, Washington, D.C., Nov. 26, 2001, 2 pages.

* cited by examiner

DETECTION OF CONTAMINATION OF MUNICIPAL WATER DISTRIBUTION SYSTEMS

The United States Government has rights in this invention pursuant to Contract No. DE-AC52-07NA27344 between the United States Department of Energy and the Lawrence Livermore National Security, LLC for the operation of Lawrence Livermore National Laboratory.

CROSS-REFERENCE TO RELATED APPLICATIONS

This application claims the benefit of U.S. Provisional Patent Application No. 60/459,750 filed Apr. 1, 2003 and titled "Technology to detect and communicate contamination of the municipal water distribution system." U.S. Provisional Patent Application No. 60/459,750 filed Apr. 1, 2003 and titled "Technology to detect and communicate contamination of the municipal water distribution system" is incorporated herein by this reference and U.S. patent application Ser. No. 10/797,986 filed Mar. 11, 2004 and titled "Detection of Contamination of Municipal water distribution systems." U.S. patent application Ser. No. 10/797,986 filed Mar. 11, 2004 and titled "Detection of Contamination of Municipal water distribution systems" is incorporated herein by this reference.

BACKGROUND

1. Field of Endeavor

The present invention relates to detection and more particularly to detection of contamination of municipal water distribution systems.

2. State of Technology

A news release on Nov. 26, 2001, *Water Supplies Need Better Protection* by Richard G. Luthy, Copyright© 2003 National Academy of Sciences, provides the following state of technology information, "The United States' water supply systems are among the greatest engineering accomplishments of the past century. Large investments by local, state, and federal government agencies led to many improvements in the supply, treatment, and distribution of water. The payoff has been great strides in improving public health. Protecting water sources and installing treatment plants virtually eliminated the most deadly waterborne diseases such as typhoid and cholera. Today, we enjoy the safest drinking water in the world. But since the terrorist acts on September 11, questions have arisen about the vulnerability of our water systems to deliberate attacks. In addition, many components are aging and need replacement. Thus, in the context of today's war on terrorism, both the infrastructure and protection of water systems must be considered in a new light. Safeguarding water supplies from sabotage will require engineering analysis and problem-solving, scientific advances, and evaluation of institutional arrangements and water policies. Top priority should be given to protecting physical water storage and transmission structures that serve large populations. Many dams, aqueducts, and pumping stations that capture and convey water over long distances are especially vulnerable to physical damage and would be difficult to replace."

The bulletin, *National Infrastructure Protection Center Terrorist Interest in Water Supply and SCADA Systems*, Information Bulletin 02-001 29, Jan. 2002, provides the following state of technology information. "A computer that belonged to an individual with indirect links to USAMA BIN LADIN contained structural architecture computer programs that suggested the individual was interested in structural engineering as it related to dams and other water-retaining structures . . . . In addition, US law enforcement and intelligence agencies have received indications that Al-Qa'ida members have sought information on Supervisory Control And Data Acquisition (SCADA) systems available on multiple SCADA-related Web sites. They specifically sought information on water supply and wastewater management practices in the US and abroad. There has also been interest in insecticides and pest control products at several Web sites."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The terrorist acts on September 11 have raised questions about the vulnerability of our water systems to deliberate attacks. US law enforcement and intelligence agencies have received indications that Al-Qa'ida members have sought information on US water supply and wastewater systems. Also the water systems are aging creating vulnerability.

The present invention provides a system for the detection of contaminates of a fluid in a conduit. The conduit is part of a fluid distribution system. The system comprises a chemical or biological sensor array connected to the conduit. The sensor array produces an acoustic signal burst in the fluid upon detection of contaminates in the fluid. A supervisory control system connected to the fluid and operatively connected to the fluid distribution system signals the fluid distribution system upon detection of contaminates in the fluid. In various embodiments of the invention the sensor is a sensor for detecting biochemicals or sporulated bacteria or viral organisms or microbial organisms or elemental chlorine or oxidative oxy-halogen compounds or ozone or oxygen or peroxydisulfate or strong reducing agents or hyposulfite or thiosulfate or sulfide or $H_2S$ or cyanide or selenium or lead sensor or mercury or arsenic or nerve agents or blistering or VX or Lewisite or G-agents or phosgene or gas or actinides or radioactive isotopes or radioactive iodine or radioactive cesium or radioactive strontium sensor or thorium or radioactive cobalt or radioactive thorium.

Other embodiments of the invention provide a method of detecting of contaminates of a fluid in a conduit. The method comprises sensing contaminates in the fluid in the conduit, producing an acoustic signal in the fluid in the conduit upon the sensing of contaminates in the fluid in the conduit, receiving the acoustic signal in the fluid in the conduit and signaling the fluid distribution system upon receiving the acoustic signal indicating the sensing of the contaminates in the fluid. The step of sensing contaminates in the fluid in the conduit in various embodiments comprises sensing biochemicals or sporulated bacteria or viral organisms or microbial organisms or elemental chlorine or oxidative oxy-halogen compounds or ozone or oxygen or peroxydisulfate or strong reducing agents or hyposulfite or thiosulfate or sulfide or $H_2S$ or cyanide or selenium or lead sensor or mercury or arsenic or nerve agents or blistering or VX or Lewisite or G-agents or phosgene or gas or actinides or radioactive isotopes or radioactive iodine or radioactive cesium or radioactive strontium sensor or thorium or radioactive cobalt or radioactive thorium contaminates in the fluid.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
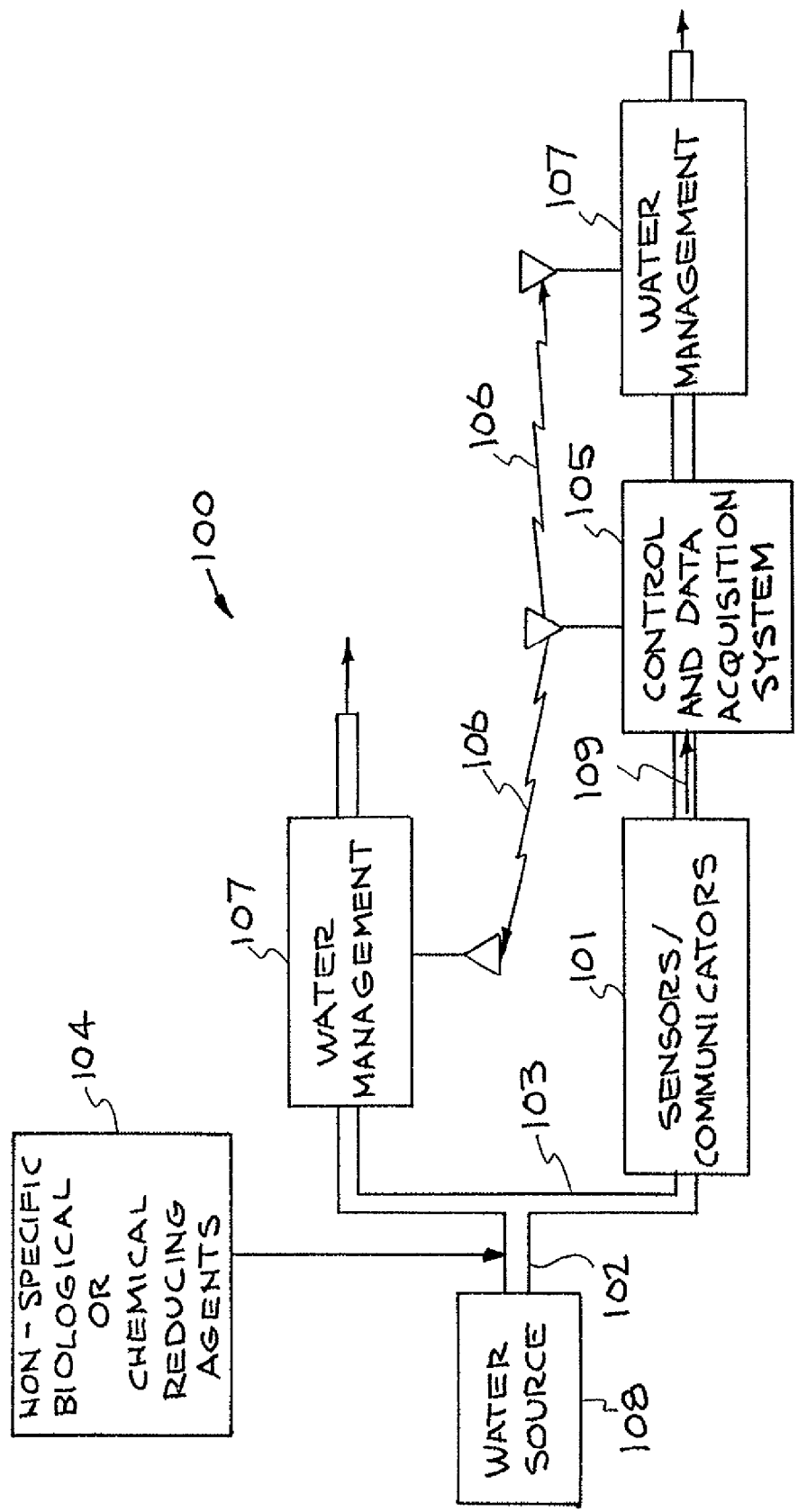
FIG. 1 illustrates an embodiment of a system constructed in accordance with the present invention.

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The terrorist acts on September 11 have raised questions about the vulnerability of our water systems to deliberate attacks. US law enforcement and intelligence agencies have received indications that Al-Qa'ida members have sought information on US water supply and wastewater systems. In addition, our water systems are aging which introduces vulnerability. The infrastructure and protection of water systems need to be considered in a new light. Safeguarding water supplies from sabotage requires engineering analysis and problem-solving, scientific advances, and evaluation of institutional arrangements and water policies.

Referring now to the drawings, and in particular to FIG. 1, an embodiment of a system constructed in accordance with the present invention is illustrated. The system is designated generally by the reference numeral 100. The system 100 provides early warning of contamination of water distribution systems. The contamination can be unauthorized contamination or accidental contamination.

The treated (i.e., chlorinated) water distribution systems are particularly vulnerable to contamination. Active chemical or biological substances could be introduced into treated water distribution mains in many ways. This could possibly be accompanied by a reducing agent that defeats the chlorination "shield" that otherwise might destroy the substances. Applicants have estimated that certain substances introduced at a point source could contaminate one million gallons each day. The system 100 is particularly useful for providing early warning of contamination in large urban areas where a typical municipal water distribution system will deliver water at a rate of 50 gal/day per capita to 350,000 individuals. Example of use of the system 100 include, use by government agencies and public agencies concerned with countering contamination of treated water.

In addition to the oxidation potential and pH sensing, the system 100 has applicability in other areas. For example, the system 100 has use for the following specific applications, it is understood there are additional uses: elemental chlorine, oxidative oxy-halogen compounds, ozone, oxygen, peroxydisulfate; strong reducing agents including hyposulfite, thiosulfate, sulfide, $H_2S$; and specific ions and solid/liquid dispersions of cyanide, selenium, lead, mercury and arsenic containing compounds; specific nerve and blistering agents including but not necessarily limited to VX, Lewisite, G-agents, phosgene, and mustard gases; and radiological sources including actinides and radioactive isotopes of iodine, cesium, strontium, thorium and cobalt. The sensors may include specific sensors for biological materials, biochemicals or live, dead or sporulated bacteriological, viral or microbial organisms. These sensors are emplaced on autonomous sensor/communicator platforms consisting of sensors, energy storage, micro-processor units, and acoustic signal generators. The energy storage unit can be comprised of batteries, primary or secondary, and in combination with power generation devices based on thermoelectric generators, hydraulic generators, fuel cells, solar, or wind converters. The system 100 includes use on non-water based systems wherein the combination of sensor and communicator may be applied to oils, molten salts, gases, and liquid metals, or other media capable of sustaining acoustic signals within a conduit or pipe.

The flow of water in mains is highly turbulent (Re~$10^5$-$10^6$). Re~$10^4$-$10^6$ Consequently, an injected contaminant rapidly forms a well mixed "plug" that maintains its initial concentration for a time that is long compared with the time of residence in the pipes. In one scenario, the sensor would detect a 30 mV drop in redox potential due to the introduction of a thiosulfate compound that neutralizes the $Cl_2$ (order of magnitude reduction in activity) and communicate it to a SCADA at the velocity of sound transmission in water (~1 mile/s). Scores of other harmful biological substances or live biological organisms would have a similar effect on redox potential, either by bulk reduction of the chlorine or by co-introduction of a chemical reducing agent that removes the chlorine shield and thus protects biological substances introduced at very low concentrations. This device detects the loss of chlorination regardless of cause, which would allow the bloom of harmful microbes normally present in water or absorbed into the slime that coats the interior of water pipes.

The system 100 includes an array of autonomous sensors/communicators 101 that are exposed to the water flow 102, from a water source 108, in pipes 103, comprising the treated (e.g., chlorinated, filtered) water municipal distribution system. The array of autonomous sensors 101 detects the loss of chlorination shield upon introduction of non-specific biological or chemical reducing agents 104 into the water 102. Each sensor communicates by emitting acoustic signal burst 109, using the pipes 103 as wave-guides or channels. The preexisting Supervisory Control and Data Acquisition Systems (SCADAS) 105 receive the signal 109 and communicate by radio 106 to water management 107.

The sensors 101 have a non-specific, broad response to the introduction of biological or chemical reducing agents into chlorinated water. The sensors 101 in one embodiment comprise a pair of electrodes: one is a Pt or graphite coated electrode; the other is a harmless reference electrode that is the type of an Ag/AgCl electrode used in medical procedures. The sensors 101 in various embodiments comprise a pair of electrodes that, under near-equilibrium conditions, output a potential proportional to the amount and strength of oxidizing material in the water. The potential or oxidation potential is not sensitive to the nature of the oxidant, and responds to all commonly used disinfectants including elemental chlorine, sodium hypochlorite, chloramines, chlorine dioxide, hydrogen peroxide or ozone, or even elemental oxygen. The sensors 101 may be enhanced by combination with pH sensors, or specific ion electrodes for elemental chlorine or other toxic ions or compounds. The sensors 101 operate as autonomous units. Each sensor will continuously measure redox potential and communicate a sudden drop to the water management through a burst 109 of encoded acoustic pulses, using the pipes 103 as wave guides or channels to confine and direct the acoustic signals.

The sensors 101 communicate by emitting acoustic signal bursts 109, using the pipes 103 as wave-guides or channels. The Supervisory Control and Data Acquisition Systems (SCADAS) 105 receives the signal 109 and communicate by radio 106 to water management 107. Systems for providing communication through fluid filled pipes are known, for example, various systems are shown in United States Patent Application No. 2002/0189362 published Dec. 19, 2002 and International Patent Application No. WO 02/103303 published Dec. 27, 2002. Both patent applications are owned by Honeywell International Inc. and were invented by Vladimar Havlena. The disclosures of United States Patent Application No. 2002/0189362 published Dec. 19, 2002 and International Patent Application No. WO 02/103303 published Dec. 27, 2002 are incorporated herein by this reference.

Power requirements for the system 100 are minimal. The oxidation potential in one embodiment is measured with a nulling potentiometer chip. Power for the acoustic transducer (a piezo-electric device) determines the power and energy requirements. In various embodiments, the power supply consists of a battery, capacitor, and/or thermoelectric collector. The power for the sensors 101 and for the acoustic transmitter 109 in various embodiments is stored in a primary battery, secondary battery or even a small fuel cell. For longest hands-off life, a secondary battery trickle charged by an internal power generator is used. The generator can for example be: a thermoelectric generator operating off the temperature difference between the water and the surrounding soil or air; an electromechanical generator converting the water flow into electric current using a propeller, water wheel; a piezo-electric device operating off the pipe water pressure or pressure difference; or streaming potential collector.

The system 100 can be installed in existing pipes through standard procedures. The system 100 is low in cost. In one embodiment only micrometer-thick layers of platinum are required. The sensor array 101 senses a drop in the oxidation potential of the water when a reducible chemical or biological substance is introduced and tends to neutralize or fully neutralizes the chlorination and communicates such a drop in potential by generating and transmitting an acoustic signal through the water 102 using the water-filled pipes 103 as wave guides and the water as the acoustic medium. The signal (e.g., a 32 bit binary code) is transmitted to pre-existing monitoring sites or Supervisory Control and Data Acquisition systems commonly called "SCADA's" (SCADA's) that are linked to water management. Each system is wireless and autonomous, being powered by a primary battery, micro fuel cell, or a secondary battery trickle charged by a thermoelectric device, solar cell, or a water-powered generator. The system 100 detects gross biological or chemical contamination, or defeat of the chlorination shield using a reducing agent (e.g., glucose, ascorbate, thiosulfate, hyposulfite, or ferrocyanide, and many other common reducing agents) preliminary to the introduction of biological or chemical agent that might be destroyed by the ca. 2 ppm ambient chlorine or chlorine-equivalent concentration.

In addition to the oxidation potential and pH sensing, the system 100 has applicability and use for: elemental chlorine, chloramines, oxidative oxy-halogen compounds, ozone, oxygen, peroxydisulfate, peroxymonosulfate; strong reducing agents including hyposulfite, thiosulfate, ferrocyanide, sulfide, $H_2S$; and specific ions and solid/liquid dispersions of cyanide, selenium, lead, mercury and arsenic containing compounds; specific nerve and blistering agents including but not necessarily limited to VX, Lewisite, G-agents, phosgene, and mustard gases; and radiological sources including actinides and radioactive isotopes of iodine, cesium, strontium, thorium and cobalt. The sensors 101 may include specific sensors for biological materials, biochemicals or live, dead or sporulated bacteriological, viral or microbial organisms. The sensors 101 are emplaced on autonomous sensor/communicator platforms consisting of sensors, energy storage, micro-processor units, and acoustic signal generators. The energy storage unit is comprised of batteries, primary or secondary, in combination with power generation devices based on thermoelectric generators, hydraulic generators, fuel cells, solar, or wind converters. The system 100 is includes non-water based applications wherein the combination of sensor and communicator may be applied to oils, molten salts, gases, and liquid metals, or other media capable of sustaining acoustic signals within a conduit or pipe.

One embodiment of the present invention provides a system for protecting municipal water supplies against neutralization of chlorine in the water and injection of a harmful substance. Potential contamination of municipal drinking water systems could include (first) neutralization of the chlorine in water pipes using thiosulfate followed by injection of a harmful substances into the thus de-chlorinated water. Plug flow would distribute the contaminated water to thousands of households.

The system 100 provides a countermeasure to this threat. The sensor array 101 monitors for redox potential. A sudden change in redox potential would indicate that the chlorine had been consumed by some organic substance, or deliberately defeated as part of a plug-flow distribution attempt. The sensor array 101 communicates an alarm to central sites 105 by sonar "pings," through the pipes 103, sending an alarm to headquarters by radio or telephone 106.

Chloramine (and in some cases, ozone) is used in water treatment; treated water has typically ~2 ppm of chlorine or some chlorine equivalent. One reducing agent is sodium thiosulfate (used to de-chlorinate tropical fish tank water; also chemically similar to sodium hyposulfite, $Na_2S_2O_3.5H_2O$, the pentahydrate of sodium thiosulfate, used to fix photographic prints and commonly called "hypo") through the following reaction (8 equivalents per reaction). For sodium thiosulfate, $4Cl_2+5H_2O+Na_2S_2O_3=2Na\ HSO_4+8HCl$.

The mass of 158 g of sodium thiosulfate is needed to neutralize 284 g of chlorine. The solubility of sodium thiosulfate in hot water (100° C.) is 2310 g/1000-g-water. Thus one liter of concentrated sodium thiosulfate will remove the chlorine from approximately 1 million liters of water: (2310 g-$Na_2S_2O_3$/Liter-conc)/[(158/284)(0.002 g-Cl/liter water)]=2.08 $10^6$ liters.

One hundred (100) gallons of saturated solution could in principle de-chlorinate 100 million gallons of drinking water.

One embodiment of the system 100 utilizes inexpensive redox sensors (consisting of a graphite or Pt micro electrode and a cheap reference electrode) 101 that are distributed within the water system at vulnerable points. A sudden change of redox potential (from chlorine oxidizing levels to reducing) indicates either an exhaustion of the chlorine or a deliberate neutralization. The sensors 101 communicate to data collection sites 105 by, e.g., encoded sonar-like "pings" through the water pipes 103, and thence to headquarters via telephone or radio 106. The collection sites currently exist. Most municipal water districts have some distributed specific ion electrodes for chlorine and other ions, [distributed as part of the "SCADA"] 105, linked by radio 106. There are provisions for shutting down a main upon loss of pressure. Other embodiments of the system 100 include network sensors such as, but not limited to, nuclear radiation, pH changes, specific ion electrodes for inorganic poisons, micropore filters for bacteria, etc. Nerine Cherepy adds fungal toxins to the list, which is not readily treated by chlorine.

Figure 2:
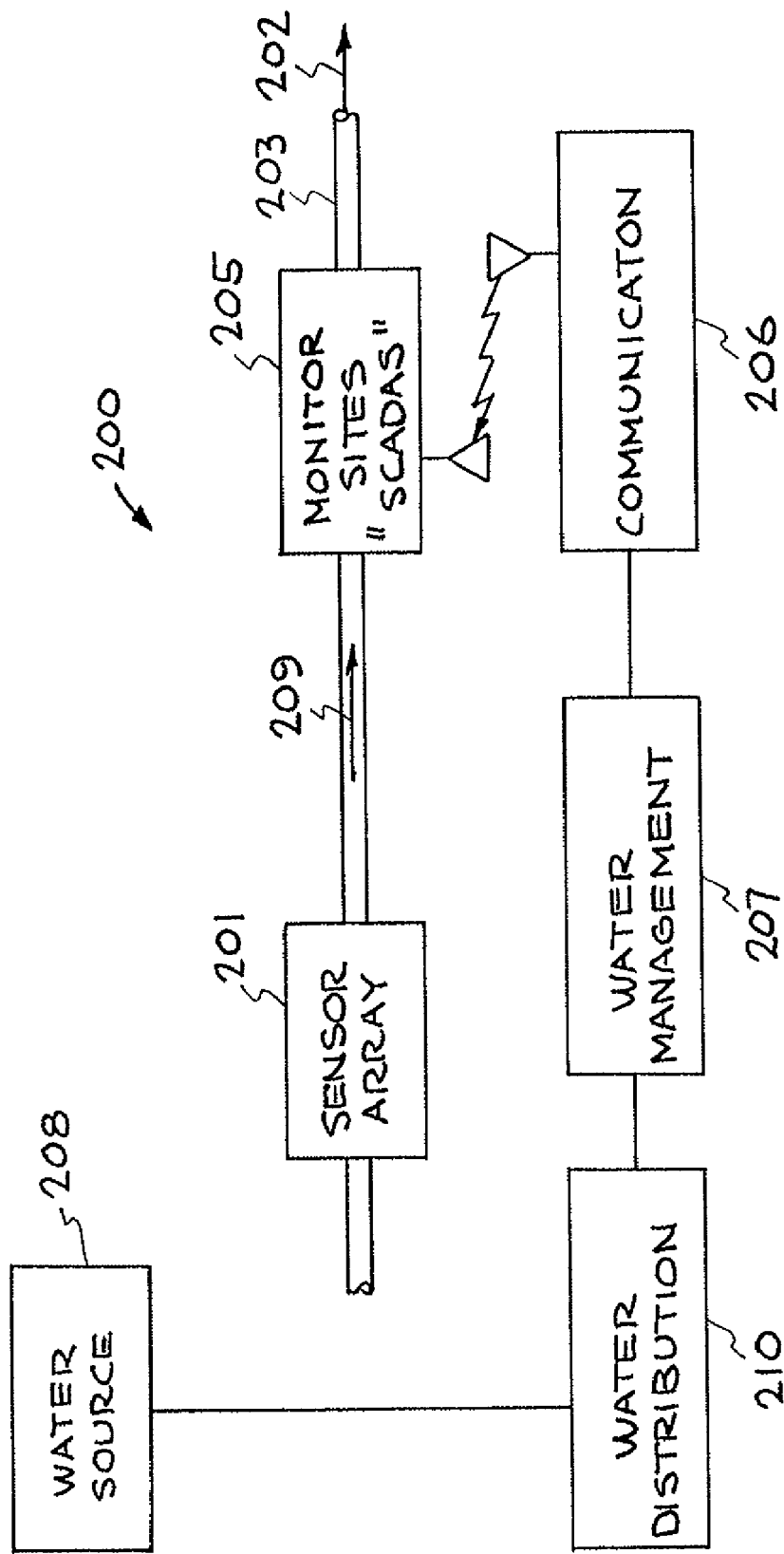
FIG. 2 illustrates another embodiment of a system constructed in accordance with the present invention.

Referring now to FIG. 2, another embodiment of a system constructed in accordance with the present invention is illustrated. The system is designated generally by the reference numeral 200. The system 200 provides early warning of contamination of water distribution systems. The contamination can be unauthorized contamination or accidental contamination.

Treated (i.e., chlorinated) water distribution systems are particularly vulnerable. Active chemical or biological agents could be introduced into treated water distribution mains in many ways (including, for example, back-flushing through household taps) possibly accompanied by a reducing agent to defeat the chlorination "shield" that otherwise might destroy the agent. The flow of water in mains is fully-developed and in most cases highly turbulent (Re~$10^4$-$10^6$). Consequently, an injected contaminant rapidly forms a well mixed "plug" that maintains its initial concentration for a time that is long compared with the time of residence in the pipes.

The system 200 uses an autonomous sensor array 201 for rapid detection of accidental or criminal contamination. The sensor array 201 detects a drop in redox potential when the water encounters any reducible chemical and/or biological substance. The change in oxidation potential is communicated by encoded acoustic signals 209 from the sensor array 201 through the water and pipes 203 to pre-existing monitor sites ("SCADAS") 205 that are radio-linked to water management 207. The system 200 provides a system for the detection of contaminates of a fluid in a pipe. The contamination can be unauthorized contamination or accidental contamination.

The system 200 useful in municipal water distribution systems for the detection of chemical or biological agent introduced by terrorists. There are innumerable biological agents and fouling substances that could be injected into water distribution systems downstream of treatment plants. Concentrated cultures of organisms that induce typhoid, cholera, plague, or Staphylococcal enterotoxin B disease have been considered plausible possibilities. The chlorine shield would be overwhelmed by organic matter when introduced in sufficiently high quantities. Potential agents as aflotoxin and sporulated *B. anthracis* are not readily killed by low levels of chlorination. However, even without being killed, these materials can cause a change in the redox potential by consuming the 2 ppm chlorination by oxidation of certain functional groups common to all proteins. The addition of a reducing agent alone would stimulate a bloom of whatever flora preexisted in the water pipes, the walls of which are normally home to slimes containing inactive or segregated flora of many types.

The system 200 is also useful in municipal water distribution systems for the detection of natural causes for a loss of chlorination, such as pipe rupture and entrainment of environmental biological material, accidental chemical contamination, or accidental overwhelming of the normal chlorination level. The system 200 also will detect the loss of redox potential associated with dissolved chlorine, chlorine dioxide, ozone or chloramines agents, etc., commonly used to disinfect potable water.

The system 200 has specific applications including the detection of elemental chlorine, oxidative oxy-halogen compounds, ozone, oxygen, peroxydisulfate; strong reducing agents including hyposulfite, ascorbate, thiosulfate, sulfide, H2S; and specific ions and solid/liquid dispersions of cyanide, selenium, lead, mercury and arsenic containing compounds; specific nerve and blistering agents including but not necessarily limited to VX, Lewisite, G-agents, phosgene, and mustard gases; and radiological sources including actinides and radioactive isotopes of iodine, cesium, strontium, thorium and cobalt. The sensors may include specific sensors for biological materials, biochemicals or live, dead or sporulated bacteriological, viral or microbial organisms. These sensors are emplaced on autonomous sensor/communicator platforms consisting of sensors, energy storage, micro-processor units, and acoustic signal generators. The energy storage unit can be comprised of batteries, primary or secondary, and in combination with power generation devices based on thermoelectric generators, hydraulic generators, fuel cells, solar, or wind converters. The system 200 includes use on non-water based systems wherein the combination of sensor and communicator may be applied to oils, molten salts, gases, and liquid metals, or other media capable of sustaining acoustic signals within a conduit or pipe. It is to be understood there are additional uses of the system 200.

The functional dependence of sensor array 201 potential on the concentration of biological reducing agents for common biologically active strains or surrogates was measured. The response time of sensor array 201 to oxidation potential was also measured upon addition of biological agents to tap water. The response time to additions of chemical reducing agents was also measured for common materials that might be used to destroy chlorination. Tap water chlorination was measured in units of ppm "chlorine equivalent." The actual chlorination materials, e.g., chloramines, elemental chlorine, chlorine dioxide, and ozone have different signals and response times, although all are qualitatively similar. The fouling of the electrodes by accumulation of biofilm-generated slime was considered and anti-fouling agents (such as copper, certain organics) are commonly available and can be used with sensor array 201. The simplest way to prevent biofouling of the Platinum redox sensor is to locate it in a strongly flowing part of the water stream in the pipe, e.g., away from the walls.

The acoustic communication uses acoustic signal bursts 209 in the fluid. Water is an ideal medium for transmitting acoustic signals, as evidence by long-wavelength communication between whales over thousands of miles. The dissipation rates of acoustic signals in water pipes as functions of frequency, temperature and salinity are considered. Signal extraction from ambient noise requires interpretative algorithms. The availability, cost and power requirements of alternative piezo-electric or electromagnetic signal generators was assessed.

The sensors 201 operate as autonomous units. Each sensor will continuously measure redox potential and communicate a sudden drop to the water management through a burst 209 of encoded acoustic pulses, using the pipes 203 as wave guides. Systems for providing communication through fluid filled pipes are known, for example, various systems are shown in United States Patent Application No. 2002/0189362 published Dec. 19, 2002 and International Patent Application No. WO 02/103303 published Dec. 27, 2002. Both patent applications are owned by Honeywell International Inc. and were invented by Vladimar Havlena. The disclosures of United States Patent Application No. 2002/0189362 published Dec. 19, 2002 and International Patent Application No. WO 02/103303 published Dec. 27, 2002 are incorporated herein by this reference.

Power requirements for the system 200 are minimal. The oxidation potential in one embodiment is measured with a nulling potentiometer chip. Power for the acoustic transducer (a piezo-electric device) determines the power and energy requirements. In various embodiments, the power supply consists of a battery, capacitor, and/or thermoelectric collector. The power for the sensors 201 and for the acoustic transmitter 209 in various embodiments are stored in a primary battery, secondary battery or even a small fuel cell or fuel battery running off an internal fuel such as iron or zinc and an oxidant in the water, or the water itself. For longest hands-off life, a secondary battery trickle charged by an internal power generator is used. The generator can for example be: a thermoelectric generator operating off the temperature difference between the water and the surrounding soil or air; an electromechanical generator converting the water flow into electric current using a propeller, water wheel; a piezo-electric device operating off the pipe water pressure or pressure difference; or streaming potential collector.

The system 200 can be installed in existing pipes through standard procedures. The system 200 is low in cost. In one embodiment only monolayers very thin, 100-1000 nanometer thick layers, of platinum are required. The sensor array 201 senses a drop in the oxidation potential of the water when a reducible chemical or biological substance is introduced and neutralizes the chlorination and communicates such a drop in potential by generating and transmitting an acoustic signal through the water 202 using the water-filled pipes 203 as wave guides and the water as the acoustic medium. The signal (e.g., a 32 bit binary code) is transmitted to pre-existing monitoring sites (SCADA's) that are linked to water management. Each system is wireless and autonomous, being powered by a primary battery, micro fuel cell, or a secondary battery trickle charged by a thermoelectric device, solar cell, or a water-powered generator. The system 200 detects gross biological or chemical contamination, or defeat of the chlorination shield using a reducing agent (e.g., thiosulfate, hyposulfite, or ferrocyanide) preliminary to the introduction of biological or chemical agent that might be destroyed by the ca. 2 ppm ambient chlorine concentration.

In addition to the oxidation potential and pH sensing, the system 200 has applicability and use for: elemental chlorine, oxidative oxy-halogen compounds, ozone, oxygen, peroxydisulfate; strong reducing agents including hyposulfite, thiosulfate, sodium ascorbate, sulfide, H2S; and specific ions and solid/liquid dispersions of cyanide, selenium, lead, mercury and arsenic containing compounds; specific nerve and blistering agents including but not necessarily limited to VX, Lewisite, G-agents, phosgene, and mustard gases; and radiological sources including actinides and radioactive isotopes of iodine, cesium, strontium, thorium and cobalt. The sensors 201 may include specific sensors for biological materials, biochemicals or live, dead or sporulated bacteriological, viral, microbial organisms, or prions. The sensors 201 are emplaced on autonomous sensor/communicator platforms consisting of sensors, energy storage, micro-processor units, and acoustic signal generators. The energy storage unit is comprised of batteries, primary or secondary, in combination with power generation devices based on thermoelectric generators, hydraulic generators, fuel cells, solar, or wind converters. The system 200 includes non-water based applications wherein the combination of sensor and communicator may be applied to oils, molten salts, gases, and liquid metals, or other media capable of sustaining acoustic signals within a conduit or pipe.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of providing early warning of contamination of water in a municipal water distribution system having existing pipes by detecting chemical or biological agent contaminates introduced into the water wherein the existing pipes are existing water filled pipes extending from a water source and wherein the municipal water system includes a supervisory control and data acquisition system and a water management system, comprising the steps of:

installing a chemical or biological sensor array in the existing pipes wherein said sensor array produces an acoustic signal burst in the water in the water filled pipes, sensing the chemical or biological agent contaminates that have been introduced into the water using said sensor array, producing an acoustic signal in the water in the existing water filled pipes upon the sensing of the chemical or biological agent contaminates that have been introduced into the water by said sensor array, using the existing water filled pipes as wave-guides or channels for transmitting said acoustic signal, receiving said acoustic signal in the existing water filled pipes wherein said acoustic signal has been transmitted using the existing water filled pipes as wave-guides or channels, and signaling the supervisory control and data acquisition system and the water management system upon receiving said acoustic signal indicating said sensing of the chemical or biological agent contaminates that have been introduced into the water.

2. The method of providing early warning of contamination of water in a municipal water distribution system having existing pipes of claim 1 wherein said step of sensing the chemical or biological agent contaminates that have been introduced into the water using said sensor array comprises sensing biochemicals or elemental chlorine or oxidative oxy-halogen compounds or ozone or oxygen or peroxydisulfate or strong reducing agents or hyposulfite or thiosulfate or sulfide or $H_2S$ or cyanide or selenium or lead sensor or mercury or arsenic or nerve agents or blistering or VX or Lewisite or G-agents or phosgene or gas or actinides or radioactive isotopes or radioactive iodine or radioactive cesium or radioactive strontium sensor or thorium or radioactive cobalt or radioactive thorium chemical contaminates that have been introduced into the water using said sensor array.

3. The method of providing early warning of contamination of water in a municipal water distribution system having existing pipes of claim 1 wherein said step of sensing the chemical or biological agent contaminates that have been introduced into the water using said sensor array comprises sensing sporulated bacteria or viral organisms or microbial organisms biological contaminates that have been introduced into the water using said sensor array.

* * * * *